(12) United States Patent
Weber et al.

(10) Patent No.: US 8,652,793 B2
(45) Date of Patent: Feb. 18, 2014

(54) SOLID PHASE-BOUND ELASTASE-BINDING ASSAY FOR THE MEASUREMENT OF ALPHA₁-ANTITRYPSIN ACTIVITY

(75) Inventors: Alfred Weber, Vienna (AT); Andrea Engelmaier, Vienna (AT); Hans-Peter Schwarz, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/455,979

(22) Filed: Apr. 25, 2012

(65) Prior Publication Data

US 2012/0322090 A1 Dec. 20, 2012

Related U.S. Application Data

(66) Substitute for application No. 61/490,553, filed on May 26, 2011.

(51) Int. Cl.
*G01N 33/53* (2006.01)
*G01N 33/547* (2006.01)
*C12Q 1/37* (2006.01)

(52) U.S. Cl.
USPC .............. 435/7.92; 435/7.1; 435/23; 436/532

(58) Field of Classification Search
None
See application file for complete search history.

(56) References Cited

PUBLICATIONS

Goodrazi et al. Decreased branching, increased fucosylation and changed sialylation of alpha-1-proteinase inhibitior in breast and ovarian cancer. Clinica Chimica Acta 1995, vol. 236, pp. 161-171.*

Brower, M.S. et al., "Alpha-1-Antitrypsin-Human Leukocyte Elastase Complexes in Blood: Quantification by an Enzyme-Linked Differential Antibody Immunosorbent Assay and Comparison With Alpha-2-Plasmin Inhibitor-Plasmin Complexes," *Blood*, May 1983, vol. 61,, No. 5, pp. 842-849.

Immunodiagnostik: "alpha-1-Antitrypin ELISA KIT for the in vitro determinatin of alpha-1-Antitrypsin in stool," Mar. 31, 2001, retrieved from <<www.biosupply.com.uk./doc.pho?id=5523>>, pp. 16-31.

International Search Report for International Patent Application No. PCT/EP2012/001768 mailed Aug. 8, 2012, 4 pages.

Karnaukhova, E. et al., "Development and evaluaton of an ELISA for quantification of human alpha-1-proteinase inhibitor in complex biological mixtures," *Biologicals*, 2007, vol. 35, pp. 285-295.

Lim, Y-P. et al., "Affinity purification and enzymatic cleavage of inter-alpha inhibitor proteins using antibody and elastase immobilized on CIM monolithic disks," *Journal of Chromatography A*, 2005, vol. 1065, pp. 39-43.

Satoh, S. et al., "The Dual Nature of the Reaction Between Porcine Elastase and Human Plasma $\alpha_1$ Proteinase Inhibitor," *Biochemical and Biophysical Research Communications*, Jan. 15, 1979, vol. 86, No. 1, pp. 130-137.

Shen, B. et al., "Biosensor analysis of the molecular interactions of pentosan polysulfate and of sulfated glycosaminoglycans with immobilized elastase, hyaluronidase and lysozyme using surface plasmon resonance (SPR) technology," *Journal of Pharmaceutical and Biomedical Analysis*, 2003, vol. 31, pp. 83-93.

\* cited by examiner

*Primary Examiner* — Shafiqul Haq
(74) *Attorney, Agent, or Firm* — Morgan, Lewis & Bockius LLP (57) ABSTRACT

The present invention relates to a method for the measurement of active alpha₁-proteinase inhibitor (A1PI) in a sample, comprising the steps of binding elastase to a solid support, letting the A1PI contained in the sample bind to the solid phase-bound elastase, and detecting solid phase-bound A1PI with a detection reagent.

8 Claims, 8 Drawing Sheets

SOLID PHASE-BOUND ELASTASE-BINDING ASSAY FOR THE MEASUREMENT OF ALPHA₁-ANTITRYPSIN ACTIVITY

CROSS-REFERENCES TO RELATED APPLICATIONS

The present application claims priority to U.S. Provisional Application Ser. No. 61/490,553, filed on May 26, 2011, the disclosure of which is hereby expressly incorporated by reference in its entirety for all purposes.

FIELD OF THE INVENTION

The present invention relates to a method for the measurement of active alpha$_1$-proteinase inhibitor (A1PI) in a sample, comprising the steps of binding elastase to a solid support, letting the A1PI contained in the sample bind to the solid phase-bound elastase, and detecting solid phase-bound A1PI with a detection reagent.

BACKGROUND OF THE INVENTION

Human alpha$_1$-proteinase inhibitor (A1PI; also: alpha-1-antitrypsin) circulates at serum levels of 20 to 48 µM. The 51 kDa glycoprotein consists of 394 amino acids with three complex type N-glycans attached to asparagines 46, 83 and 247. Different N-glycan branching and truncation of the N-terminus result in a characteristic pattern on isoelectric focusing. In addition, a C-terminal truncated form of A1PI which misses the C-terminal lysine after cleavage by basic carboxypeptidases was described recently. A1PI is a member of the superfamily of serpins (serine proteinase inhibitors). Its anti-protease activity absolutely requires the active site Met358-Ser359. This site occupies an exposed loop on the molecule and tightly binds the active region of neutrophil elastase or other serine proteases including trypsin, cathepsin G, plasmin, thrombin and tissue kallikrein. A1PI exerts a preferential inactivating function for neutrophil elastase since the association rate constant for the A1PI/neutrophil elastase complex is 25-fold higher than those measured for other serine proteases. A1PI diffuses from plasma into the lung, where it is responsible for more than 90% of the anti-elastase protection of the lower respiratory tract. Deficiency of A1PI, leading to plasma concentrations below 20 µM, leaves the lung poorly protected and highly vulnerable to progressive lung destruction. Therapy is directed towards the replacement or augmentation of plasma A1PI.

The measurement of A1PI neutrophil elastase inhibitory activity was basically made possible as early as 1974 when the synthesis of the chromogenic substrate N-succinyl-L-alanyl-L-alanyl-L-alanin-p-nitroanilide (Suc(Ala)$_3$-pNA) was described. This substrate has a high selectivity for elastase. Trypsin and chymotrypsin for example have hydrolysis rates of 0.007 and 0.014, respectively, when measured at the same concentration as elastase and setting the rate obtained with elastase to 100. At pH 8.0 and 25° C., the substrate Suc-(Ala)$_3$-pNA has the kinetic constants $K_m$ and $K_{cat}$ of 1.15 mM and 18.6 s$^{-1}$ for elastase, respectively. Its selectivity and good solubility in water were the basis for an A1PI elastase inhibition assay as firstly described in 1981. This assay was based on the measurement of residual elastase activity of A1PI samples which have been incubated with an excess of elastase. Briefly, samples were incubated with a defined amount of porcine elastase for a defined time before the chromogenic substrate was added. The release of pNA was monitored photometrically and allowed to calculate the residual activity of elastase, which itself is inversely proportional to the A1PI activity of the sample. Standard assay formats using this chromogenic approach have a relatively high limit of quantification of about 3 µg/mL active A1PI. Although the sensitivity of such assay formats can be increased by using fluorogenic substrates for the measurement of residual elastase, they are still limited by the fact that one of the excess reaction partners, i.e. elastase, and not the reaction product is measured.

Therefore, a strong need exists to provide a novel assay for the determination of A1PI activity in a sample having improved sensitivity.

This need is satisfied by providing the embodiments characterized in the claims.

SUMMARY OF THE INVENTION

The present invention describes the use of solid phase-bound elastase for measuring the anti-elastase inhibition activity of A1PI in a sample. The amounts of elastase-A1PI complex formed are then directly measured by detecting elastase-complexed, plate-bound A1PI with a detection reagent instead of measuring residual elastase activity. This mode of detection advantageously increases the assay's sensitivity by a factor of 1,000. The superior selectivity of the assay depends on the specificity of the elastase-A1PI complex formation, which is not changed after binding elastase to a solid support, and on the specificity of the detection reagent used.

In particular, the present invention relates to a method for the measurement of active alpha$_1$-proteinase inhibitor (A1PI) in a sample, comprising the steps of binding elastase to a solid phase, incubating the solid phase with the sample, incubating the solid phase with a detection reagent specifically binding to A1PI, determining the amount of detection reagent bound to the solid phase, and determining the amount of active A1PI in the sample.

DETAILED DESCRIPTION OF THE INVENTION

In one aspect, the present invention relates to a method for the measurement of active alpha$_1$-proteinase inhibitor (A1PI) in a sample, comprising the steps of
(a) binding elastase to a solid phase;
(b) incubating the solid phase with the sample;
(c) incubating the solid phase with a detection reagent binding to A1PI;
(d) determining the amount of detection reagent bound to the solid phase; and
(e) determining the amount of active A1PI in the sample.

In this context, "measurement of active A1PI in a sample" as used herein refers to the determination of the amount and/or the concentration of active A1PI that is contained in a sample. Further, "active A1PI" as used herein refers to A1PI that is capable of exerting its native function, i.e. binding and inactivating elastase and other serine proteases.

The elastase used in the method of the present invention is not particularly limited and can be e.g. human or porcine elastase. Means for binding elastase to a solid phase are known in the art and are not particularly limited. They include for example the incubation of the solid support with elastase in a suitable buffer, e.g. phosphate-buffered saline (PBS), for an appropriate length of time, e.g. overnight, at an appropriate temperature, e.g. +4° C. Further suitable buffers and incubation parameters are known in the art.

The solid phase on which the method of the present invention is performed is not particularly limited. Moreover, suitable solid phases are known in the art. In a preferred embodiment, the solid phase is a microplate, e.g. a microplate having an absorptive surface such as e.g. a NUNC™ Maxisorp plate.

In the context of the present invention, elastase can be attached to the solid phase by adsorption, where it is retained by hydrophobic forces. Alternatively, the surface of the solid phase can be activated by chemical processes that cause covalent linkage of the elastase to the support.

If the solid phase is silicon or glass, the surface must generally be activated prior to attaching the elastase. Activated silane compounds such as triethoxy amino propyl silane, triethoxy vinyl silane, and (3-mercapto-propyl)-trimethoxy silane can be used to introduce reactive groups such as amino, vinyl, and thiol groups, respectively. Such activated surfaces can be used to link the elastase directly (in the cases of amino or thiol), or the activated surface can be further reacted with linkers such as glutaraldehyde, bis(succinimidyl)suberate, SPPD (succinimidyl 3-[2-pyridyldithio]propionate), SMCC (succinimidyl-4-[N-maleimidomethyl]cyclohexane-1-carboxylate), SLAB (succinimidyl[4-iodoacetyl] aminobenzoate), and SMPB (succinimidyl 4-[1-maleimidophenyl]butyrate) to separate the elastase from the surface. Vinyl groups can be oxidized to provide a means for covalent attachment. Vinyl groups can also be used as an anchor for the polymerization of various polymers such as poly-acrylic acid, which can provide multiple attachment points for elastase. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons), or Ficoll (molecular weight 70,000 daltons). Additionally, polyelectrolyte interactions can be used to immobilize elastase on the solid phase.

The solid phase can be any suitable material with sufficient surface affinity to bind elastase. Useful solid supports include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials can be used as filters with the above polymeric materials); and mixtures or copolymers of the above classes, such as graft copolymers obtained by initializing polymerization of synthetic polymers on a pre-existing natural polymer. Nitrocellulose and nylon can also be used. All of these materials can be used in suitable shapes, such as films, sheets, tubes, particulates, or plates, or they can be coated onto, bonded, or laminated to appropriate inert carriers, such as paper, glass, plastic films, fabrics, or the like.

Alternatively, the solid phase can constitute microparticles. Appropriate microparticles can be selected by one skilled in the art from any suitable type of particulate material and include those composed of polystyrene, polymethylacrylate, polypropylene, latex, polytetrafluoroethylene, polyacrylonitrile, polycarbonate, or similar materials. Further, the microparticles can be magnetic or paramagnetic microparticles, so as to facilitate manipulation of the microparticle within a magnetic field.

Microparticles can be suspended in the mixture of reagents and sample or can be retained and immobilized by a support material. In the latter case, the microparticles on or in the support material are not capable of substantial movement to positions elsewhere within the support material. Alternatively, the microparticles can be separated from suspension in the mixture of reagents and sample by sedimentation or centrifugation. When the microparticles are magnetic or paramagnetic the microparticles can be separated from suspension in the mixture of reagents and sample by a magnetic field.

Incubation of the solid phase with the sample according to the present invention can be performed at suitable temperatures for a suitable length of time, e.g. for 60 minutes at room temperature. Further suitable time/temperature combinations are known to a person skilled in the art.

In a preferred embodiment, the solid phase is blocked prior to incubating the solid phase with the sample in step (b), in order to decrease unspecific adsorption of A1PI or other sample components to the solid phase. Suitable blocking agents are known in the art and are not particularly limited. They include for example bovine serum albumin (BSA), methylated BSA, human serum albumin, casein, hydrolyzed casein, nonfat dry milk, gelatin or milk powder in suitable buffers. A suitable blocking buffer is for example PBS containing 0.05% polysorbate 20 and 10 mg/mL BSA. Blocking can be performed at suitable temperatures for a suitable length of time, e.g. for 60 minutes at room temperature. Further suitable time/temperature combinations are known to a person skilled in the art.

In another preferred embodiment, the sample is diluted prior to incubation with the solid phase in step (b). Suitable dilution ratios depend on the expected A1PI concentration in the sample and are known to a person skilled in the art. Further, suitable dilution buffers are known in the art and are not particularly limited. They include for example PBS.

Suitable detection reagents that can be used in the method of the present invention are known in the art and are not particularly limited. They include for example compounds, compositions or molecules capable of specifically or substantially specifically (i.e. with limited cross-reactivity) binding to an epitope of A1PI. These agents (or ligands) are typically antibodies, such as monoclonal antibodies, or derivatives or analogs thereof, but also include, without limitation: Fv fragments; single chain Fv (scFv) fragments; Fab' fragments; F(ab')$_2$ fragments; humanized antibodies and antibody fragments; camelized antibodies and antibody fragments; chimeric antibodies; and multivalent versions of the foregoing. Multivalent capture agents also can be used, as appropriate, including, without limitation: monospecific or bispecific antibodies; such as disulfide stabilized Fv fragments. These agents also include, without limitation, aptamers, synthetic peptides, binding molecules, nucleic acids, etc. and are as known in the art. Suitable labels for the detection reagents to be used in the method of the present invention are not particularly limited and are known in the art. They include for example peroxidase, alkaline phosphatase, biotin, and fluorescent molecules. In a preferred embodiment, the detection reagent is an anti-human A1PI antibody conjugated to peroxidase.

Incubation of the solid phase with a detection reagent can be performed at suitable temperatures for a suitable length of time, e.g. for 60 minutes at room temperature. Further suitable time/temperature combinations are known to a person skilled in the art. Further, suitable dilution ratios and buffers for diluting the detection reagent prior to incubation are known in the art and can be easily determined.

In a preferred embodiment, the solid phase is washed prior to and after incubating the solid phase with the detection reagent in step (c). Suitable washing buffers are known in the art and are not particularly limited. They include for example PBS containing 0.05% polysorbate 20.

Means for determining the amount of detection reagent bound to the solid phase are known in the art and are not particularly limited. In the case of peroxidase-labeled antibody conjugates, they include for example the incubation of the solid phase with a suitable chromogenic peroxidase substrate, e.g. the ready-to-use trimethylbenzidine peroxidase reagent SureBlue (KPL), at a suitable temperature, e.g. at room temperature, for a sufficient amount of time to allow color formation. Subsequently, color formation can be stopped, e.g. by addition of 1.5 M sulfuric acid, and the amount of formed color determined, e.g. in an ELISA reader at 450 nm. Further suitable chromogenic substrates, incubation times and temperatures, and means for measuring the amount of formed color are known to a person skilled in the art. Amplification system commonly used in the art, including the biotin-avidin system, can also be employed in the context of the present invention.

Finally, means for determining the amount of active A1PI in the sample are known in the art and are not particularly limited. They include for example the correlation of sample data to a suitable calibration curve that is e.g. established using known A1PI concentrations.

The present invention will be further illustrated in the following examples without any limitation thereto.

EXAMPLES

Example 1

Preparation and Characteristics of a 6-Point Assay Calibration Curve

The assay calibration curve consisting of six serial 1+1 dilutions of a working standard preparation covered an A1PI activity concentration range from 110 ng/mL to 3.5 ng/mL. The curve was obtained as follows:

Porcine elastase (Roche, 11027905001; 50 mg/mL) was diluted to 50 µg/mL with phosphate-buffered saline (PBS; 8 g/L NaCl; 0.2 g/L KCl; 0.2 g/L $KH_2PO_4$; 1.26 g/L $Na_2HPO_4$× $2H_2O$; native pH) and incubated with the wells of a NUNC Maxisorp F96 plate at 4° C. overnight (100 µL/well). The plate was then washed with PBS containing 0.05% Polysorbate 20 (washing buffer; WB) and inactivated by incubation with 200 µL/well washing buffer containing 10 mg/mL bovine serum albumin (dilution buffer; DB) at 37° C. for 60 min. 100 µL/well dilution buffer was added to the wells and the pre-diluted standard, control or samples were loaded and serially diluted directly on the plate. The wells B11 and B12 contained only dilution buffer and served as blanks. The plate was then incubated at room temperature (RT; 20 to 25° C.) for 60 min and washed afterwards. Then, sheep anti-human A1PI peroxidase (The Binding Site), diluted 1/1,000 in DB, was applied to the wells at 100 µl/well, incubated at RT for 60 min and removed by a washing step. The washed plate was then incubated with the ready-to-use trimethylbenzidine peroxidase reagent SureBlue (KPL; 100 µL/well) and incubated at RT until appropriate color development. The reaction was then stopped with 100 µL/well of 1.5 M sulfuric acid. Within 60 min, the plate was then measured in an ELISA reader at 450 nm with a reference measurement at 620 nm.

The standard preparation used for the assay calibration was a purified A1PI preparation, calibrated with a validated chromogenic elastase inhibition assay against the actual WHO standard for A1PI. Thus, the concentration assigned to this working standard was 22.1 mg active A1PI per mL. The final dilution series, prepared in duplicate, consisted of the six dilutions 1/200,000 to 1/6,400,000, resulting in an A1PI activity range from 110 ng/mL to 3.5 ng/mL. The calibration curve was finally obtained by using a log-log fitting of the blank-corrected optical densities (ODs) measured and the A1PI activity concentrations of the assay calibrators.

Figure 1:
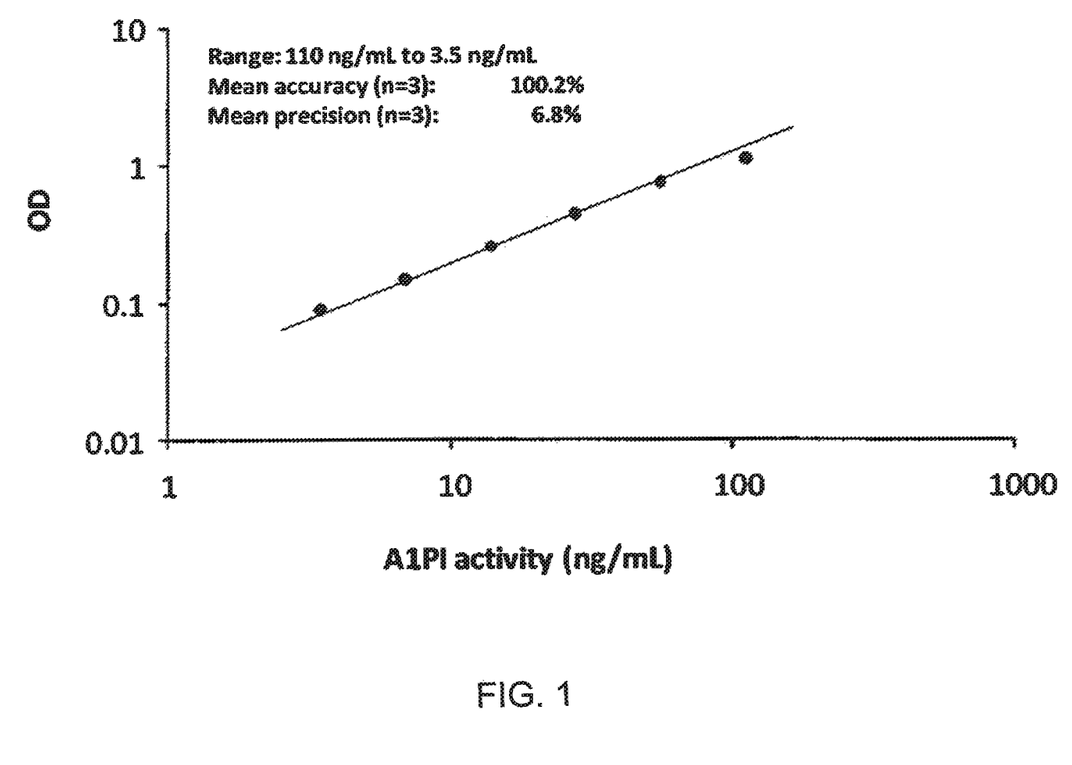
FIG. 1 shows a representative 6-point calibration curve obtained as the mean of three curves prepared on one day.

FIG. 1 shows a representative 6-point calibration curve obtained as the mean of three curves prepared on one day. The calibration curve characteristics slope, y-intercept and correlation coefficient were very similar for all three curves averaged. This was true also for the accuracy and the precision of the curves. The calibration curves met accepted requirements for accuracy, precision and linearity and were thus deemed to be appropriate for extrapolating samples. The range of linear relation between signal and A1PI activity concentration went down to 3.5 ng/mL. Thus, the assay was 1000-times more sensitive than the chromogenic standard elastase inhibition assay relying on the measurement of residual elastase activity.

Example 2

Measurement of the A1PI Activity of Human Plasma

Plasma contains several other proteinase inhibitors apart from A1PI which theoretically could interact with elastase. The association constant for the A1PI-elastase complex, however, has been reported to be about 25-times higher than those measured for other proteinase inhibitors. Thus, A1PI exerts a preferential inhibitory effect for elastase.

Figure 2:
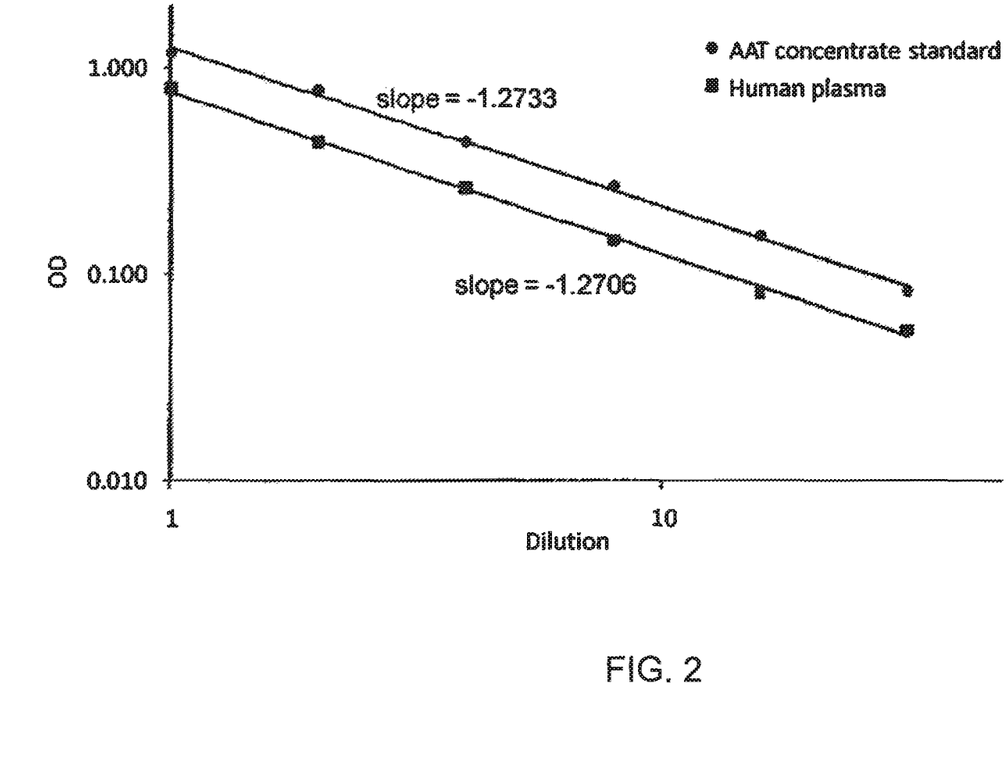
FIG. 2 shows the dose-response curves for two A1PI preparations with different purity.

Nevertheless, the dose-response curves for a purified A1PI preparation, used as an assay standard, and a human reference plasma preparation was compared. The latter preparation was measured in a dilution series comprising the six serial 1+1 dilutions 1/20,000 to 1/640,000. FIG. 2 shows the dose-response curves for the two preparations with different purity. The two dose-response curves were very similar as shown by their slopes which differed by less than 0.5%. This finding demonstrates that immobilizing elastase to the solid support did not change its selectivity for binding A1PI.

Example 3

Measurement of Samples Containing Aggregated A1PI

An aggregated A1PI preparation was obtained by heating a solution of purified A1PI with a concentration of 20 mg/mL at 60° C. for 15 min. This solution was then mixed with native A1PI in different ratios. Several mixtures containing 10 to 90% of heat-aggregated A1PI in native A1PI were prepared and analyzed together with the native and the heat-aggregated A1PI by native polyacrylamide gel electrophoresis (PAGE; cf. FIG. 3) and by high-performance size-exclusion chromatography (HP-SEC; cf. FIG. 4).

Figure 3:
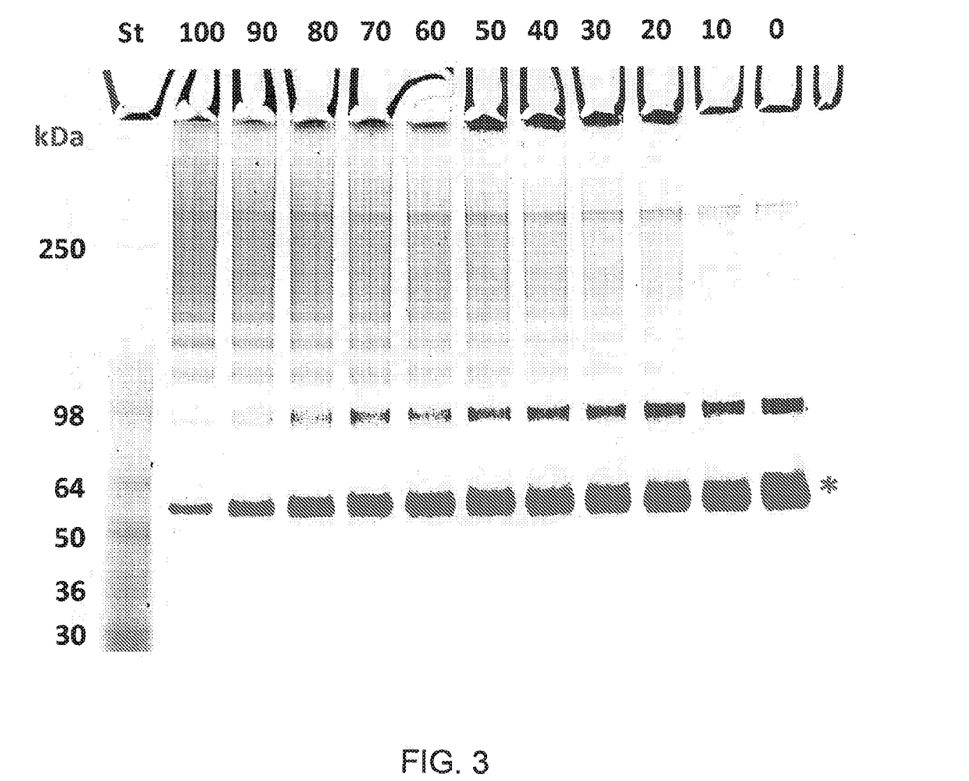
FIG. 3 shows a polyacrylamide gel electrophoresis of an aggregated A1PI preparation.
Figure 4:
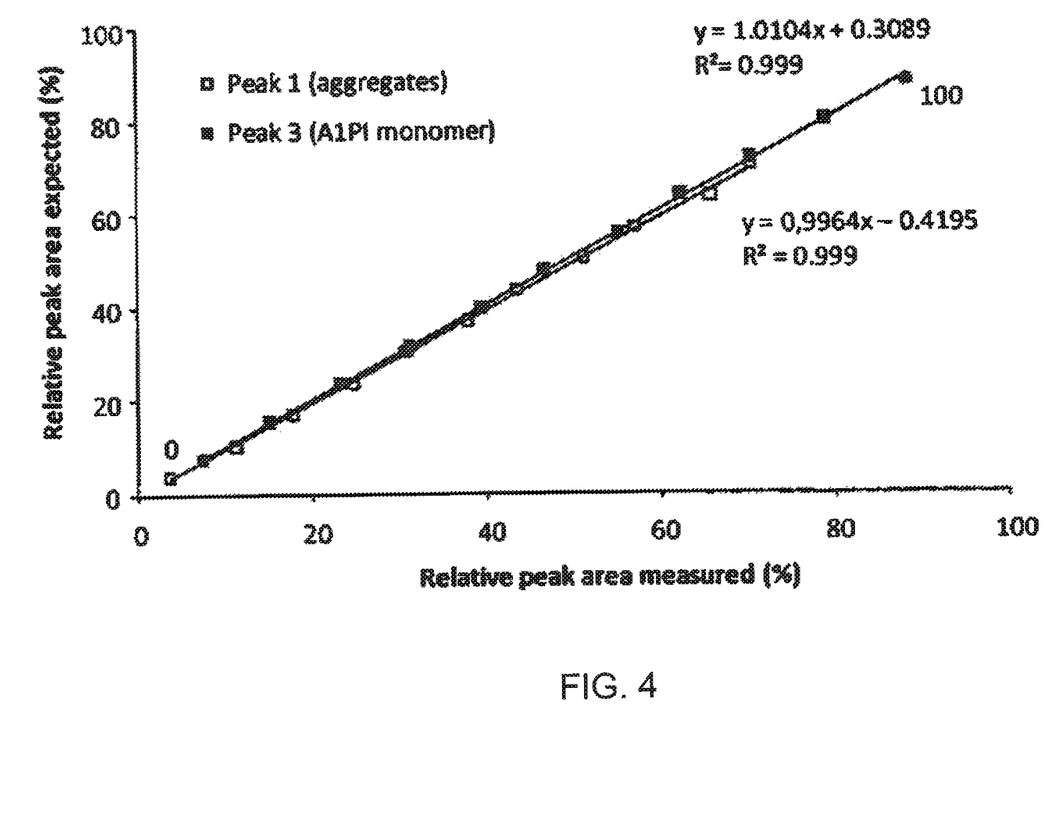
FIG. 4 shows a high-performance size-exclusion chromatography of an aggregated A1PI preparation.

The numbers on the top of the gel shown in FIG. 3 indicating the different samples give the relative levels of heat-aggregated A1PI in the mixtures as a percentage, whereas the star marks the band corresponding to the A1PI monomer. The samples, loaded at the same protein concentration and stained with Coomassie, obviously differ in the intensity of the A1PI monomer band, which is inversely proportional to the relative levels of heat-aggregated A1PI in the samples. On the other hand, the high molecular weight sample compounds increase with the relative levels of heat-aggregated A1PI in the mixtures. Thus, native PAGE clearly confirms the heat-induced aggregation of A1PI. This finding was also confirmed by the data of the HP-SEC analyses, where higher relative levels of heat-aggregated A1PI in the mixtures correlated with higher relative peak areas of the aggregate peak and lower relative peak areas of the A1PI monomer.

Figure 5:
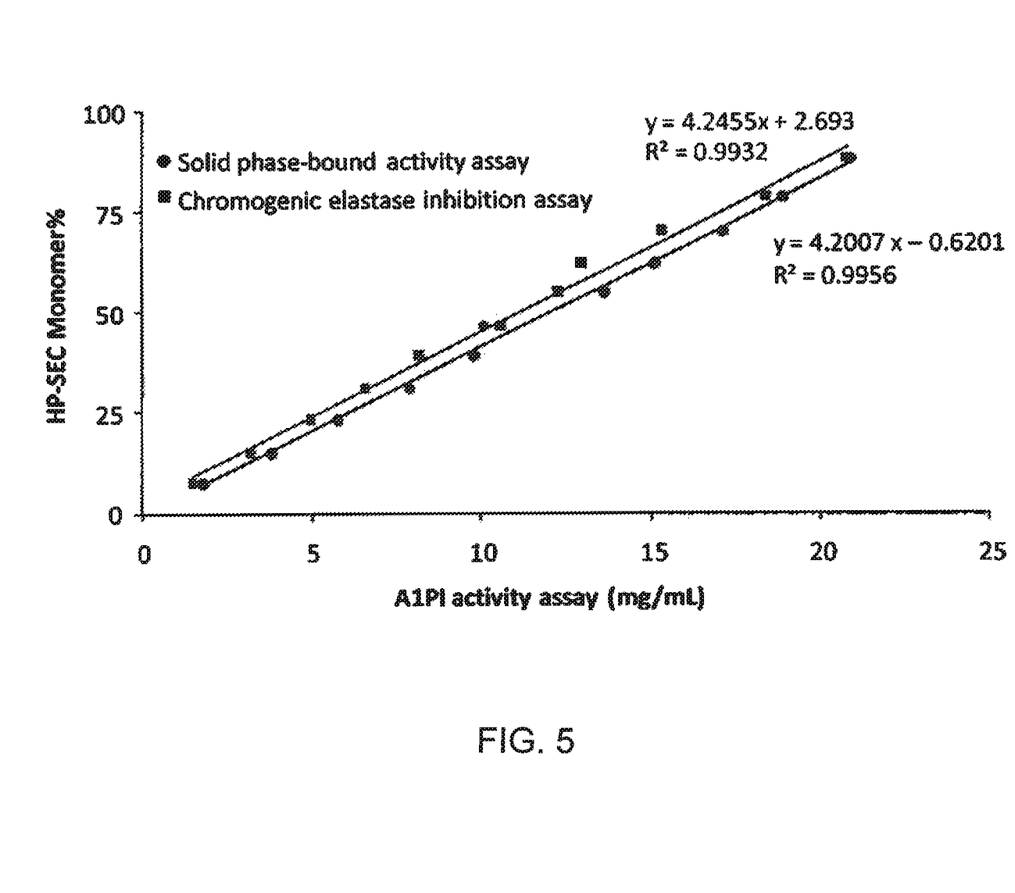
FIG. 5 shows the correlation between the A1PI monomer levels, determined with HP-SEC, and the results of two different activity assays measured for the samples with different concentrations of A1PI aggregates.

FIG. 5 shows the correlation between the A1PI monomer levels, determined with HP-SEC, and the results of the two activity assays measured for the samples with different concentrations of A1PI aggregates. The A1PI activity of these samples was measured using the chromogenic elastase inhibition assay and the solid-phase bound elastase A1PI activity assay of the present invention. The A1PI activity, measured with the chromogenic elastase inhibition assay, clearly correlated with the relative levels of A1PI monomers as shown by the squared correlation coefficient of $R^2=0.9932$ found for the regression curve. This could be expected because the formation of A1PI aggregates predominantly involves the active site of A1PI, absolutely mandatory for its inhibitory activity. The same good correlation was found when the solid phase-bound elastase A1PI activity assay of the present invention was used to measure the A1PI activity of the samples. In addition, both regression curves showed similar slopes which differed only by 1%.

These data confirmed that the solid phase-bound elastase A1PI assay of the present invention measured the elastase inhibition activity of A1PI. They furthermore demonstrated that even high concentrations of inactive, aggregated A1PI did not interfere with the solid phase-bound elastase A1PI activity assay of the present invention. Clearly, these data show that the plate-bound elastase A1PI activity assay only measures active A1PI, i.e. A1PI that is able to inhibit elastase.

Example 4

Figure 6:
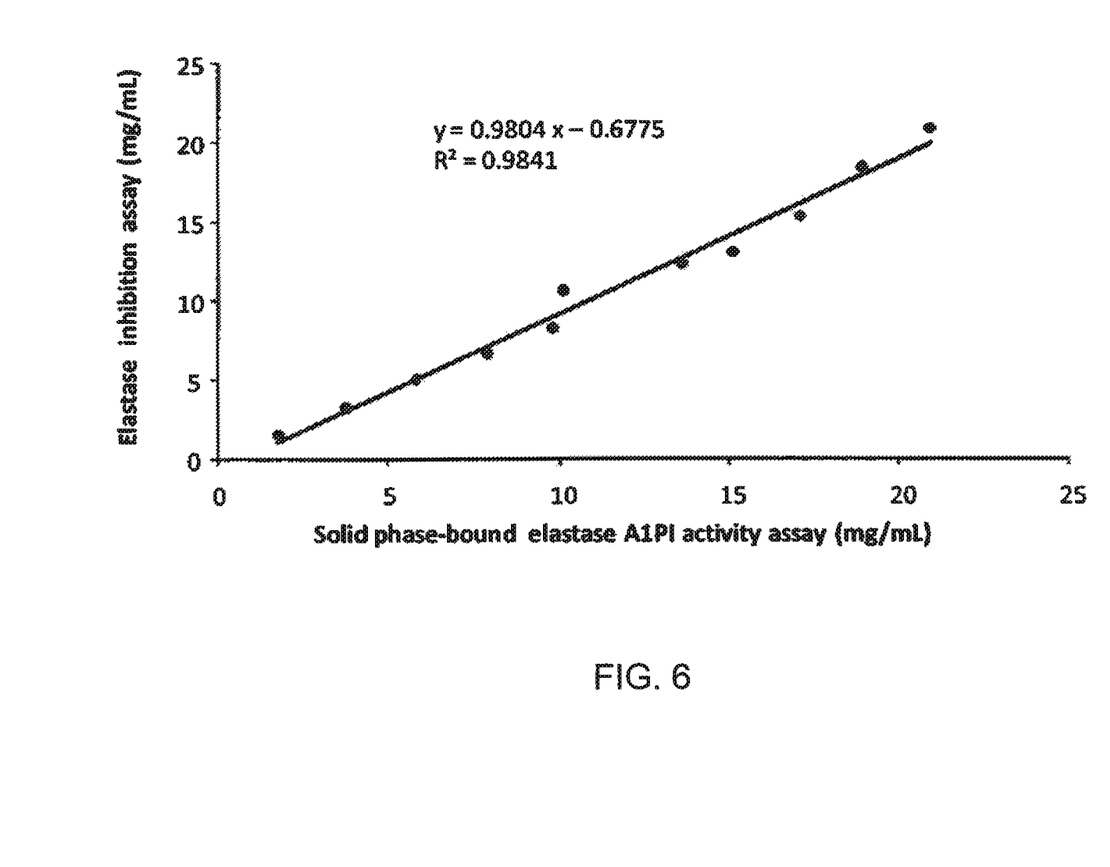
FIG. 6 shows the regression curve obtained by plotting the results of two different activity assays.

Correlation Between the Chromogenic Elastase Inhibition Assay and the Solid Phase-Bound Elastase A1PI Activity Assay A1PI samples containing defined, increasing levels of heat-aggregated A1PI were measured with the chromogenic elastase inhibition assay, which relies on incubating the A1PI samples with an excess of porcine elastase and measuring residual elastase activity with the chromogenic substrate Suc-{Ala}$_3$-pNA. Elastase splits the chromogenic substrate and releases pNA, which is measured photometrically. The optical density is directly proportional to the elastase concentration, which itself is inverse proportional to the A1PI activity within defined ranges. In addition, these samples were measured with the solid phase-bound elastase A1PI activity assay of the present invention. FIG. 6 shows the regression curve obtained by plotting the results of the two activity assays.

The A1PI activity concentrations measured with the two assays correlated well over the activity range investigated, namely 2 to 20 mg active A1PI/mL as demonstrated by the squared correlation coefficient of $R^2=0.98$. These data demonstrated the equivalence of the solid phase-bound elastase A1PI activity of the present invention with the chromogenic elastase inhibition assay because the differences in A1PI concentrations measured for the samples investigated reflected rather analytical random-caused variance than a systematic one. Both assays were shown to specifically measure active A1PI. In particular, 10-times higher concentrations of inactive A1PI were shown not to interfere with both assays.

Example 5

Measurement of Oxidized A1PI

The A1PI proteinase inhibitory activity absolutely requires the active site Met358-Ser359. This site occupies an exposed loop on the molecule and tightly binds the active region of neutrophil elastase. Met358 is sensitive to oxidation resulting in an inactivation of A1PI, resulting in a loss of its elastase inhibitory activity.

The specificity of the solid phase-bound elastase A1PI activity assay of the present invention was shown by measuring oxidized A1PI which was obtained by the following procedure. Briefly, 1.5 mL of a purified, fully active A1PI preparation with an A1PI concentration of 20 mg/mL were diluted with 13.5 mL 50 mM $KH_2PO_4$ buffer, pH 5.0, containing 100 mM KCl and 1 mM $MgCl_2$. 5.1 mL $H_2O_2$ were added to cause oxidation. This reaction mixture was incubated at RT for 2 h and then dialyzed against phosphate-buffered saline at 4° C. overnight. Aliquots were prepared and stored frozen at −20° C. Table 1 gives the results of the analyses done. In particular, the A1PI protein was measured with an ELISA. Furthermore, the A1PI activity was measured with a chromogenic elastase inhibition assay and the plate-bound elastase A1PI activity assay of the present invention.

TABLE 1

Analyses of the oxidized A1PI preparation

| Sample | Protein (mg/mL) | Chromogenic elastase inhibition assay | | Solid phase-bound elastase assay | |
|---|---|---|---|---|---|
| | | mg/mL | % | mg/mL | % |
| Oxidized A1PI | 1.55 | <0.009 | <0.6 | 0.003 | 0.2 |

Figure 7:
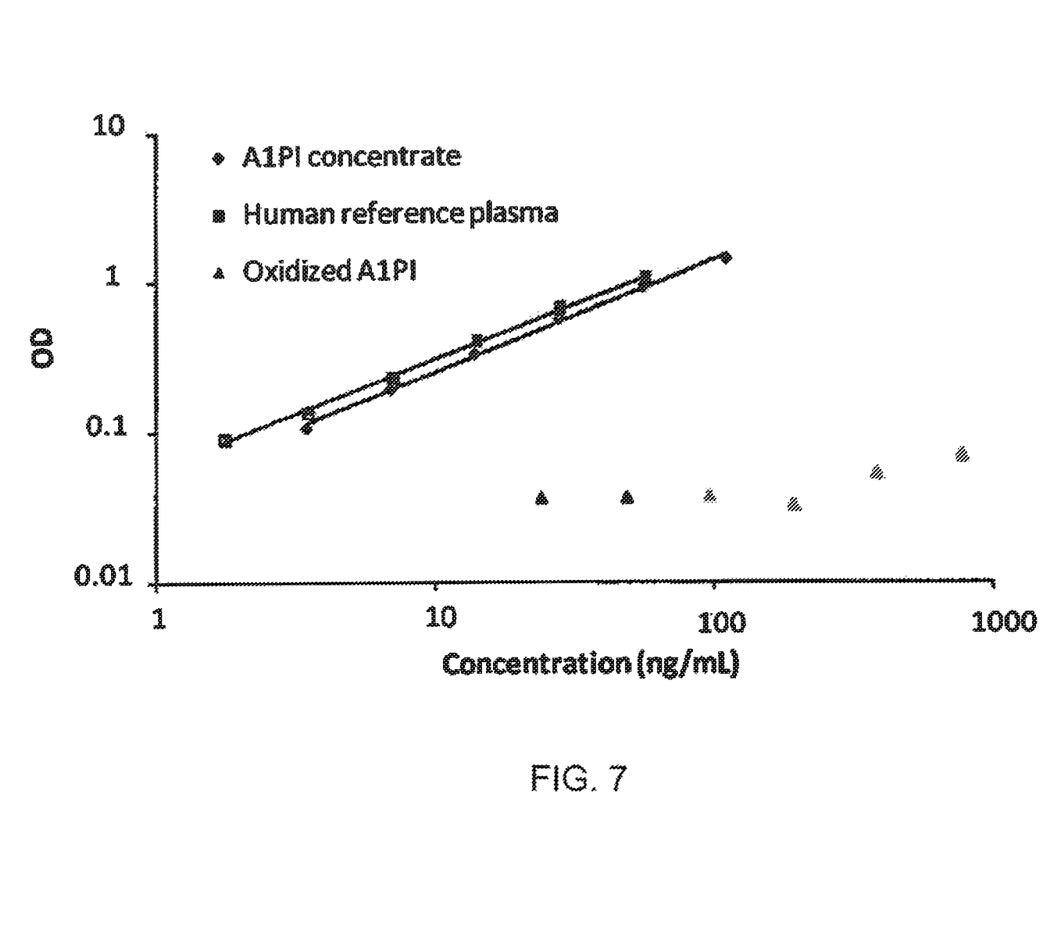
FIG. 7 shows the concentration-response curves obtained with the solid phase-bound elastase A1PI activity assay for a purified A1PI concentrate, a human reference plasma preparation and an oxidized A1PI preparation.

The A1PI protein measurement with an ELISA resulted in an A1PI protein concentration of 1.55 mg/mL which agreed well with the expected when the dilution caused by the procedure was considered. In contrast, the chromogenic elastase inhibition assay did not detect active A1PI and a concentration of below 0.009 mg/mL was measured for the oxidized A1PI. This corresponded to less than 0.6% of the initial activity. These data were in line with the results of the solid phase-bound elastase assay of the present invention, where only 0.2% of the initial activity was found for this preparation. Overall, these data further demonstrated that the specificity of the solid phase-bound elastase A1PI activity assay of the present invention was similar to that of the chromogenic elastase inhibition assay. Oxidized A1PI, which remained fully immune-reactive as shown by the data of the ELISA, did not show considerable activity independent of whether measured with the chromogenic elastase assay or the solid phase-bound elastase assay. FIG. 7 shows the concentration-response curves, obtained with the solid phase-bound elastase A1PI activity assay, for a purified A1PI concentrate, a human reference plasma preparation and the oxidized A1PI preparation. The concentration-response curves clearly evidence that the solid phase-bound elastase A1PI activity assay of the present invention only measures active A1PI since the oxidized A1PI gave only very low signals which could indicate the presence of low levels of still native A1PI.

Example 6

Measurement of Elastase-A1PI Complexes

Inhibition of elastase by A1PI results in the formation of a stable A1PI-elastase complex and A1PI loses its inhibitory activity after being bound to elastase. Consequently, A1PI-elastase complexes should not be detected or interfere with an A1PI activity assay. Therefore, a purified A1PI preparation was incubated with different amounts of a purified human elastase preparation to obtain samples containing different levels of A1PI-elastase complexes.

Briefly, a purified A1PI preparation was diluted with 20 mM Tris-HCl, pH 8.2, containing 10 mg/mL human serum albumin, to a concentration of 400 µg/mL and incubated with a human neutrophil elastase preparation (ICN, 191337; 500 µg/mL) at different molar ratios at RT for 45 min. In particular, samples with molar ratios between A1PI and elastase of 1:0.26, 1:0.52, 1:1.02 and 1:2.55 were prepared and further analyzed. Table 2 shows the results of the measurement of the A1PI activity with the solid phase-bound elastase A1PI activity assay of the present invention.

TABLE 2

Solid phase-bound elastase A1PI activity assay of A1PI-elastase complex-containing samples

| | Molar ratio | Solid phase-bound elastase A1PI activity assay | |
|---|---|---|---|
| Sample | A1PI:elastase | mg/mL | % initial |
| 1 | 1:0.00 | 20.1 | 100.0 |
| 5 | 1:0.26 | 15.4 | 76.6 |
| 4 | 1:0.51 | 10.7 | 53.2 |

TABLE 2-continued

Solid phase-bound elastase A1PI activity assay of A1PI-elastase complex-containing samples

| | Molar ratio | Solid phase-bound elastase A1PI activity assay | |
|---|---|---|---|
| Sample | A1PI:elastase | mg/mL | % initial |
| 3 | 1:1.02 | <0.6 | <3 |
| 2 | 1:2.55 | <0.6 | <3 |

Incubating the purified A1PI preparation with increasing concentrations of neutrophil elastase reduced the A1PI activity measured with the solid phase-bound elastase A1PI activity assay of the present invention. The mixture containing an equimolar concentration of A1PI and elastase showed no measurable activity. In contrast, the samples with molar ratios between A1PI and elastase of 1:0.51 and 1:0.26, still had A1PI activity with concentrations corresponding to 53.2% and 76.6% of that measured for the sample before complex formation. This closely matched the loss of activity expected to be induced by the levels of elastase added. These findings also demonstrated the ability of the solid phase-bound elastase A1PI activity assay of the present invention to measure the elastase inhibition activity of A1PI.

Example 7

Amidolytic Activity of Plate-Bound Elastase

The method of the present invention depends on the complex formation between plate-bound elastase and A1PI. It is therefore mandatory that the plate-bound elastase retains its activity, since only active enzyme will attack the reactive center loop of A1PI resulting in complex formation. The chromogenic substrate Suc-$(Ala)_3$-pNA was used to measure the elastase solution after the coating procedure and to check for the presence of active elastase on the coated wells of the microplate. Thus, an elastase activity of 18.8 µg/mL was measured for the solution recovered after the coating procedure. The difference to the concentration before coating (20 µg/mL) implied that 120 ng elastase bound per well which equals a density of 1.3 ng elastase per $mm^2$. A reasonable estimate for the surface adsorption of IgG is 0.4 ng per $mm^2$. When chromogenic substrate was added to the coated and washed wells, it was found that all wells showed elastase activity resulting in the hydrolysis of the chromogenic substrate. These data confirmed that the complex formation seen after incubation with A1PI really was based on the proteolytic attack of elastase. When then the blank-corrected ODs were extrapolated on a calibration curve obtained by measuring free elastase, it was found an elastase activity of 82.3 ng per well. This meant that more than 50% of the elastase remained active after the coating procedure.

Example 8

Complex formation with other inhibitors

Figure 8:
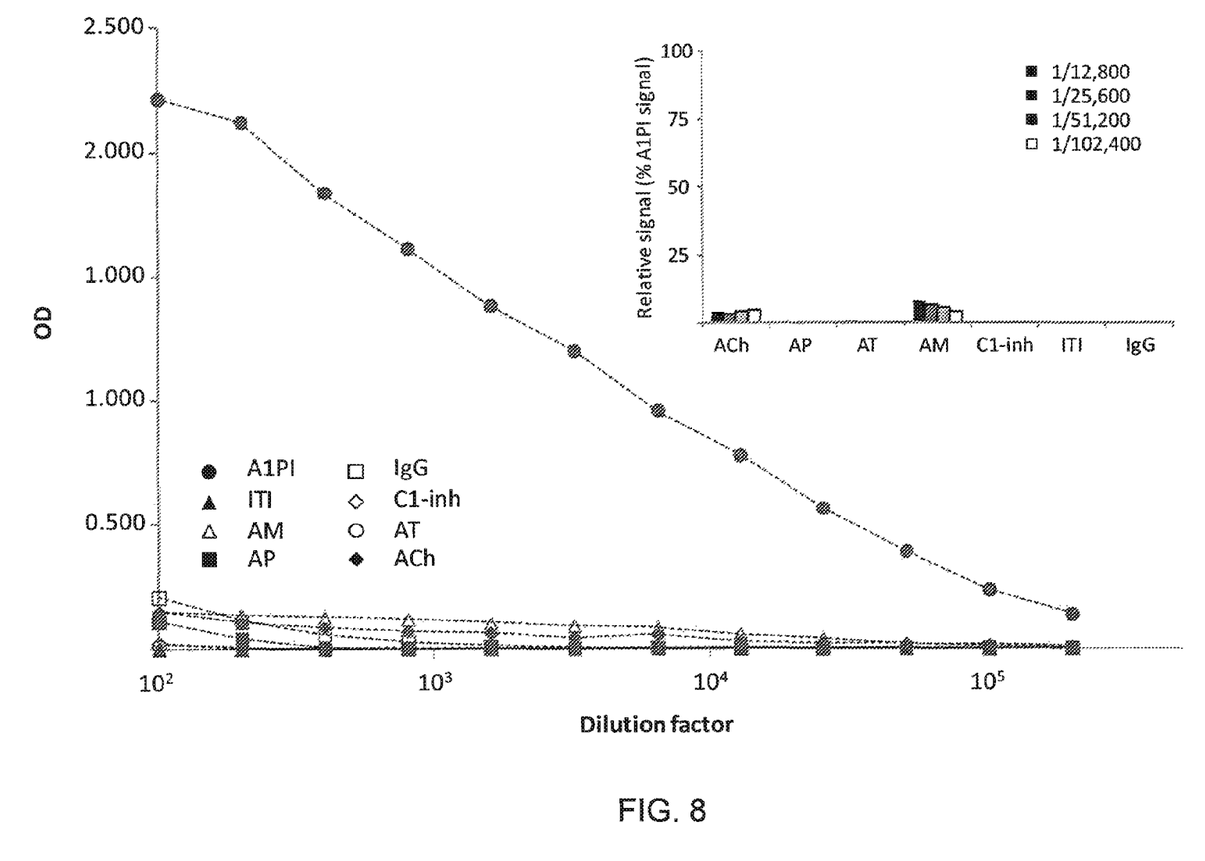
FIG. 8 shows elastase-complex formation with plasma protein inhibitors. The insert gives the relative signal intensities determined for the different inhibitors at the four dilutions given as percent of that measured for A1PI.

Human plasma contains several proteins which are able to form complexes with elastase. Although the rate constant for the complex formation between A1PI and elastase is 25-fold higher than those measured for other serine proteases, it was nevertheless investigated whether or not the presence of these other inhibitors affected the measurement of A1PI. The dose-response curves obtained for plasma and purified A1PI preparations, however, did not indicate any effect of these inhibitors as their slopes were similar. In particular, $\alpha_1$-antichymotrypsin (ACh), $\alpha_2$-antiplasmin (AP), antithrombin (AT), α2-macroglobulin (AM), C1-inhibitor (C1- inh) and inter-α-trypsin inhibitor (ITI) were checked for their capability to form substantial amounts of complexes with the plate-bound elastase and thus affect the measurement of A1PI. As an additional negative control, the level of non-specific binding to the wells was determined with plate-bound elastase using IgG as a non-specific marker protein, whereas the binding of A1PI was used as a positive reference. Table 3 gives the blank corrected mean ODs measured for the dilution series of the human reference plasma preparation 1R31003. These dilution series, comprising twelve dilutions ranging from 1/100 to 1/204,800, were incubated with the plate-bound elastase. Potentially formed complexes were then detected by using antibody peroxidase conjugates specific for the respective inhibitor. These data are also shown in FIG. 8, where the dilution versus OD curves are directly compared.

TABLE 3

Elastase-complex formation with plasma protein inhibitors

| Dilution | A1PI | ACh | AP | AT | AM | C1-inh | ITI | IgG |
|---|---|---|---|---|---|---|---|---|
| 100 | 2.214 | 0.151 | 0.111 | 0.016 | 0.150 | 0.027 | 0.000 | 0.210 |
| 200 | 2.121 | 0.107 | 0.038 | 0.008 | 0.137 | 0.005 | 0.000 | 0.113 |
| 400 | 1.839 | 0.086 | 0.000 | 0.003 | 0.129 | 0.000 | 0.000 | 0.058 |
| 800 | 1.614 | 0.072 | 0.000 | 0.001 | 0.119 | 0.000 | 0.000 | 0.030 |
| 1600 | 1.385 | 0.062 | 0.000 | 0.000 | 0.104 | 0.000 | 0.000 | 0.011 |
| 3200 | 1.203 | 0.044 | 0.000 | 0.002 | 0.092 | 0.000 | 0.000 | 0.002 |
| 6400 | 0.959 | 0.058 | 0.000 | 0.000 | 0.083 | 0.000 | 0.000 | 0.000 |

TABLE 3-continued

Elastase-complex formation with plasma protein inhibitors

| Dilution | A1PI | ACh | AP | AT | AM | C1-inh | ITI | IgG |
|---|---|---|---|---|---|---|---|---|
| 12800 | 0.779 | 0.029 | 0.000 | 0.004 | 0.059 | 0.000 | 0.000 | 0.000 |
| 25600 | 0.567 | 0.017 | 0.000 | 0.000 | 0.038 | 0.000 | 0.000 | 0.000 |
| 51200 | 0.391 | 0.017 | 0.000 | 0.000 | 0.022 | 0.000 | 0.000 | 0.000 |
| 102400 | 0.239 | 0.012 | 0.000 | 0.000 | 0.011 | 0.000 | 0.000 | 0.000 |
| 204800 | 0.141 | 0.005 | 0.000 | 0.000 | 0.006 | 0.000 | 0.000 | 0.000 |

The data clearly evidenced that A1PI forms a complex with elastase more readily than any of the other inhibitors investigated. Moderate complex formation, however, was detected for two of the six inhibitors tested for: Only the inhibitors $\alpha_2$-macroglobulin and $\alpha_1$-antichymotrypsin showed measurable formation of an elastase complex with mean signals that made up 6.0% and 3.9% of that measured for the complex formation with A1PI. In particular, the mean for the dilutions 1/12,800 to 1/102,400 was calculated to better evaluate the signals obtained for the different inhibitors. These data suggested that more than 90% of the plate-bound elastase was found in complex with A1PI on the assumption that a direct comparison was possible using the approach followed here. Only minor amounts of the other plasma proteinase inhibitors were able to compete with A1PI for the binding to the plate-bound elastase. These data are in line with the dilution-response curves determined for plasma samples and purified A1PI preparations. These curves were parallel and did not obviously differ in their slopes. In contrast, effective competition for the plate-bound elastase caused by inhibitors other than A1PI would be supposed to reduce the elastase concentration available for the reaction with A1PI. Consequently, this should lead to different slopes for the concentration-response curves dependent on the purity of the preparation investigated. In a second approach, the influence of AM was investigated in more detail. Thus, mixtures of purified A1PI and AM were prepared containing the constant A1PI concentration of 192 ng/mL and increasing concentrations of AM ranging from 0 to 2000 ng/mL. The method of the present invention was then run with these samples and the concentration-response curves obtained were compared. Table 4 gives the blank-corrected ODs of the dilution series, which were used to calculate the log-log regression curves. These curves are further described by their slopes, y-intercepts and correlation coefficients. The slopes are also given as a percent of that measured for the sample containing no AM.

TABLE 4

Analysis of mixtures of purified A1PI and AM

| A1PI | AM concentration (ng/mL) | | | | | | |
|---|---|---|---|---|---|---|---|
| ng/mL | 2000 | 1000 | 400 | 200 | 100 | 20 | 0 |
| 192.0 | 0.887 | 0.924 | 0.986 | 0.999 | 0.995 | 1.003 | 0.948 |
| 96.0 | 0.593 | 0.587 | 0.621 | 0.622 | 0.627 | 0.637 | 0.639 |
| 48.0 | 0.369 | 0.373 | 0.411 | 0.402 | 0.398 | 0.392 | 0.377 |
| 24.0 | 0.225 | 0.223 | 0.245 | 0.231 | 0.237 | 0.231 | 0.224 |
| 12.0 | 0.129 | 0.120 | 0.130 | 0.129 | 0.129 | 0.127 | 0.122 |
| a | 0.6974 | 0.7297 | 0.7188 | 0.7336 | 0.7300 | 0.7438 | 0.7430 |
| b | −1.6231 | −1.6805 | −1.6280 | −1.6594 | −1.6516 | −1.6781 | −1.6904 |
| r | 0.9983 | 0.9975 | 0.9966 | 0.9982 | 0.9981 | 0.9985 | 0.9975 |
| % slope | 93.9 | 98.2 | 96.7 | 98.7 | 98.2 | 100.1 | 100.0 |

The concentration-response curves were only slightly affected by the increased AM concentration of the mixtures because their slopes differed by less than 7% from the slope found for the sample containing zero AM. However, complex formation between AM and elastase occurred, but the amount of complex formed seemed not to interfere with the measurement of A1PI. The ten times excess in mass of AM over A1PI resulted in about equimolar concentrations but for a correct estimate of the molar ratios it has to be considered that AM contains four inhibitory active sites and that possible more than one site could be involved in binding to the plate-immobilized elastase. Such an interaction can also occur during the chromogenic assay, where AM-bound elastase will still be active when measured with a chromogenic substrate, thus contributing to an underestimation of the A1PI activity measured for a given sample. In that case, the inactivation of AM with methylamine could improve the situation. The data obtained for the method of the present invention, however, demonstrated that the purity of the samples did not bias the measurement of functionally active A1PI, even when AM was present at an equimolar concentration.

Example 9

Precision and Accuracy of the Method of the Present Invention

Accuracy and precision of the method of the present invention were determined in two sample matrices. First, samples mimicking bronchoalveolar lavage (BAL) solutions with a low total protein concentration of not higher than 50 μg/mL were prepared with functionally active A1PI concentrations ranging from 0.0002 to 0.01 mg/mL. Plasma-like samples with A1PI concentrations ranging from 0.01 to 0.8 mg/mL were obtained by diluting a human plasma reference plasma preparation with human serum albumin, whereas the sample with the concentration of 3 mg/mL was obtained by adding purified A1PI. Finally, the current $1^{st}$ WHO standard for A1PI, encoded 05/162, was also included. Accuracy was expressed as the recovery of the nominal A1PI concentration given as a percent, precision as the relative standard deviation of the mean of six measurements, done on one day (intra-assay) or on six days (inter-assay). The results are shown in Table 5 below.

TABLE 5

Precision and accuracy of the method of the present invention over a range from 0.0002 to 12.4 mg/mL functionally active A1PI

| A1PI | Accuracy | Precision | | |
|---|---|---|---|---|
| mg/mL | % Recovery | intra-run | inter-run | Sample matrix |
| 0.0002 | 85.0 | 2.4 | 3.7 | BAL-mimicking sample |
| 0.0005 | 92.8 | n.d. | 3.5 | BAL-mimicking sample |
| 0.001 | 95.0 | n.d. | 4.3 | BAL-mimicking sample |
| 0.002 | 98.4 | n.d. | 8.4 | BAL-mimicking sample |
| 0.005 | 106.8 | n.d. | 3.2 | BAL-mimicking sample |
| 0.01 | 107.4 | 1.4 | 4.1 | BAL-mimicking sample |
| 0.01 | 106.0 | 3.1 | 6.1 | Plasma-like |
| 0.10 | 104.7 | 2.6 | 7.5 | Plasma-like |
| 0.20 | 98.9 | 4.2 | 4.5 | Plasma-like |
| 0.50 | 104.9 | 2.0 | 7.0 | Plasma-like |
| 0.80 | 102.5 | 2.9 | 6.8 | Plasma-like |
| 1.00 | n.d. | 3.1 | 8.2 | Plasma-like |
| 3.00 | 94.0 | 3.1 | 5.5 | Plasma-like |
| 12.4 | 100.1 | n.d. | 8.6 | WHO standard 05/162 | n.d.: not done; BAL: bronchoalveolar lavage

The invention claimed is:

1. A method for the measurement of active alpha$_1$-proteinase inhibitor (A1PI) in a sample, comprising the steps of
   (a) binding elastase to a solid phase, wherein the elastase bound to the solid phase retains its enzymatic activity;
   (b) incubating the solid phase from step (a) with the sample; and then washing the solid phase;
   (c) incubating the solid phase from step (b) with a detection reagent specifically binding to A1PI, wherein the detection reagent comprises an A1PI epitope binding domain, and then washing the solid phase;
   (d) determining the amount of detection reagent bound to the solid phase in step (c); and
   (e) thereby determining the amount of active A1PI in the sample.

2. The method according to claim 1, further comprising the step of blocking the solid phase with bovine serum albumin prior to step (b).

3. The method according to claim 1, further comprising the step of diluting the sample prior to incubation with the solid phase in step (b).

4. The method according to claim 1, wherein the elastase is porcine elastase.

5. The method according to claim 1, wherein the solid phase is a microplate.

6. The method according to claim 1, wherein the detection reagent is conjugated to peroxidase.

7. The method according to claim 1, wherein the detection reagent is selected from an antibody, an antibody fragment, a camelized antibody, a camelized antibody fragment, a Fv fragment, a single chain Fv (scFv) fragment, a Fab' fragment, a F(ab')2 fragment, a chimeric antibody and a multivalent version or a combination thereof.

8. The method according to claim 7, wherein the detection reagent is conjugated to peroxidase.

* * * * *